United States Patent
Lavender

[19]

[11] Patent Number: 6,106,508

[45] Date of Patent: Aug. 22, 2000

[54] SEALABLE OSTOMY POUCH

[76] Inventor: Michael R. Lavender, 2015 N. Sedgwick St., Chicago, Ill. 60614

[21] Appl. No.: 09/243,654

[22] Filed: Feb. 3, 1999

[51] Int. Cl.$^7$ ........................................................ A61F 5/44
[52] U.S. Cl. ............................................................ 604/339
[58] Field of Search ................................... 604/332, 334, 604/337, 339, 342, 335, 338, 340

[56] References Cited

U.S. PATENT DOCUMENTS

| | | |
|---|---|---|
| 2,695,646 | 11/1954 | Wyk . |
| 2,841,198 | 7/1958 | Kwake . |
| 3,618,606 | 11/1971 | Brown . |
| 3,902,496 | 9/1975 | Eakin . |
| 4,084,590 | 4/1978 | Caraway . |
| 4,387,713 | 6/1983 | Calanni .................................. 604/333 |
| 4,533,354 | 8/1985 | Jensen . |
| 4,604,095 | 8/1986 | Samuelsen . |
| 4,755,177 | 7/1988 | Hill . |
| 4,786,285 | 11/1988 | Jambor . |
| 5,139,492 | 8/1992 | Leise . |
| 5,607,413 | 3/1997 | Holmberg . |

FOREIGN PATENT DOCUMENTS 1526764 of 0000 France .

*Primary Examiner*—Wynn Wood Coggins
*Assistant Examiner*—A. T. Nguyen
*Attorney, Agent, or Firm*—Robert L. Marsh

[57] ABSTRACT

An ostomy pouch has a first and second panels of flexible material sealed to each around the edges to form a bag, and a aperture for receiving waste product from a stoma. A seal i provided on the inner surfaces of the two panels to seal waste products in the pouch before the pouch is removed from the side of a wearer.

6 Claims, 3 Drawing Sheets

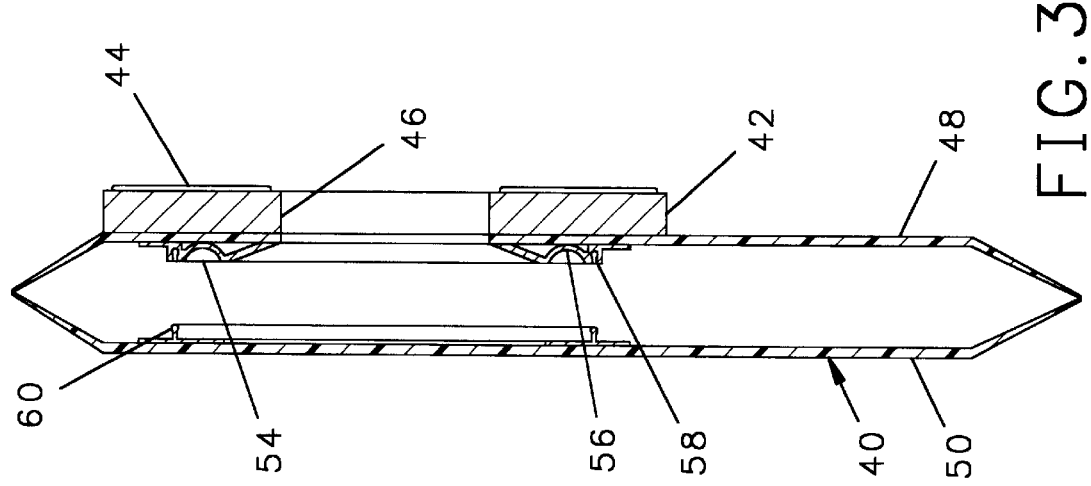
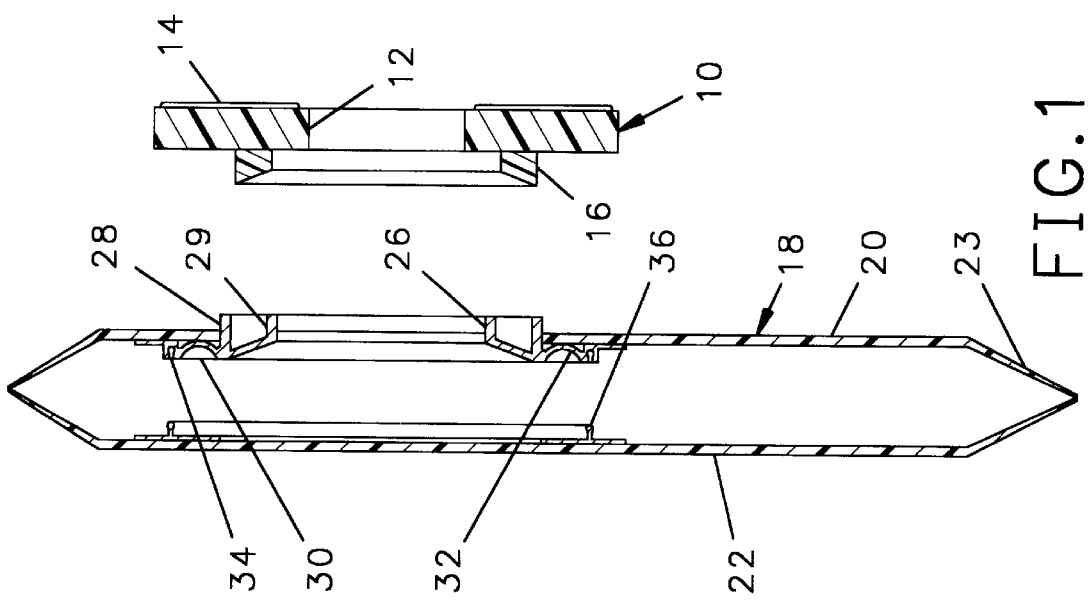

SEALABLE OSTOMY POUCH

The present application relates to ostomy pouches and in particular to a pouch in which the contents can be sealed therein prior to the removal of the pouch from a wearer.

BACKGROUND OF THE INVENTION

Ostomy pouches are used to collect human waste products by individuals who cannot eliminate body waste in a normal manner. People who suffer from certain intestinal or rectal diseases such as cancer or Crohn's disease may sometimes require a surgical procedure whereby the diseased portion of the intestine is removed and the healthy portion of the intestine is attached to the abdominal wall. The end of the intestine is inverted and stitched to the skin forming a stoma. Waste products which are discharged from the stoma are collected in an ostomy pouch. A similar procedure can be used to remove diseased portions of a urinary system whereby a urinary tube is connected to the abdominal wall and the discharge is collected in a urostomy pouch.

Ostomy pouches and urostomy pouches are bags made of two substantially planar panels of material joined at the edges thereof with an aperture in one panel sized to fit around the stoma or the urostoma. The bag is secured to the skin of the wearer by a suitable sealing material which extends around the aperture. For the purposes of this discussion, the term "ostomy pouch" shall be used to mean both ostomy pouches and urostomy pouches since the features of the invention may be used on either device.

The pouch may be designed as a single piece, having a sealing means which extends around the aperture for sealing the pouch to the skin of a wearer as part of the pouch. Such single piece pouches may have sealed lower ends such that they must be replaced after each use, or may have a drain at the lower end thereof such that the device is reusable until the wearer chooses to replace the device.

Alternately, the pouch may be manufactured in two pieces. The first piece is a substantially planar, somewhat rigid mounting portion having a central opening sized to fit around the stoma (or urostoma). The mounting portion is made of a hydrocolloid material which has adhesive properties such that it may be removably attached to the skin of a wearer. The outer surface of the first piece has a retainer for removeably retaining an ostomy pouch thereto. The ostomy pouch has a flexible wall with an opening therein to receive waste products from the stoma and an annular attachment portion around the opening which is adapted to be removeably attached to the retainer on the mounting portion. Like the one piece ostomy pouches, the lower ends of a two piece ostomy pouch may be either sealed, such that the pouch must be replaced after each use, or be drainable, such that the bag can be reused until the wearer chooses to replace it, usually at the day's end.

When the wearer of an ostomy pouch having a closed lower end desires to dispose of the waste products collected therein, the wearer must remove the pouch from his or her body and dispose of the pouch and the contents. The waste products collected in such ostomy pouches however are usually not fully decomposed because the intestinal tract of the wearer has been shortened and, as a consequence, the waste products may have a strong odor. The wearer of an ostomy pouch having a sealed lower end must therefore deal with the mess of the waste products in the ostomy pouch and the odor emitted therefrom each time the pouch is replaced. The task is unpleasant when done in the privacy of one's own home, but the problem is even more unpleasant for one making use of public facilities.

A single piece ostomy pouch having a sealed lower end typically has a hydrocolloid mounting portion with a central opening therein for fitting around the stoma. When the single piece ostomy bag is removed from the wearer's skin, the upper half of the adhesive hydrocolloid mounting portion may be folded against the lower half thereof with the adhesive of the upper and lower halves binding against each other to seal the contents within the bag for disposal. Even though the single piece bag can be sealed, the odors are so pungent that removing the pouch causes embarrassment to the wearer, especially when it is changed while in public facilities.

The wearer of a two piece ostomy pouch is unable to seal the aperture of the pouch closed because the mounting member with the adhesive surface remains adhered to his body. There presently is no adequate solution whereby the wearer of a two piece ostomy pouch can seal the pouch for disposal while using public facilities.

It would be desirable to provide an ostomy pouch having a sealed lower end which would reduce the mess and odors that presently accompany the task of removing and replacing such ostomy pouches.

SUMMARY OF THE INVENTION

Briefly, the present invention is embodied in an ostomy pouch for receiving waste products having a first flexible panel with an inner surface and an outer surface and an outer edge and a second flexible panel having an inner surface and an outer edge. At least a portion of the outer edge of the first panel is sealed to the outer edge of the second panel to form a bag or pouch. The first panel has an aperture therein sized to fit around the stoma of a wearer and an attachment means on the outer surface for attachment to the skin of a wearer whereby human waste products from the stoma may be received into the bag. The invention includes a first sealing means on the inner surface of the first panel and a second sealing means on the inner surface of the second panel, with the first and second sealing means for sealing against each other for preventing waste products in the pouch from escaping through the aperture.

In the preferred embodiment, the first and second sealing means include a ridge on the inner surface of either the first or second panel and a groove on the inner surface of the other of the first and second panel such that when the ridge is mated into the groove, the parts are sealed together. Preferably, the sealing means is an annular seal extending around the circumference of the aperture of the panel which fits against the stoma. Alternatively, the sealing means may extend across the width of the pouch to seal the lower portion thereof from the upper portion. Also, where a ridge and groove seal is provided, it is desirable that the ridge on one panel be offset with respect to the groove of the other panel such that the seal cannot inadvertently engage while the ostomy pouch is being worn.

BRIEF DESCRIPTION OF THE DRAWINGS

A better and more complete understanding of the invention will be had after a reading of the following detailed description taken in conjunction with the drawings wherein:

FIG. 1 is a side cross sectional view of a two piece ostomy pouch in accordance with one embodiment of the present invention where the pouch is separated from the mounting portion;

FIG. 3 is a cross sectional view of a one piece ostomy pouch incorporating the present invention;

DETAILED DESCRIPTION OF THE PREFERRED EMBODIMENT

Figure 5:
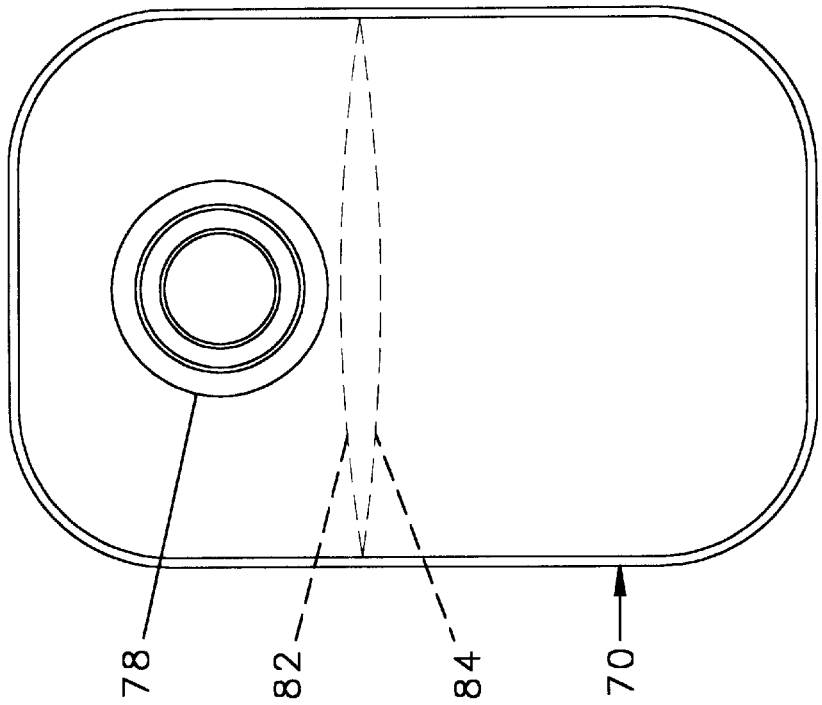
FIG. 5 is a front view of the ostomy pouch shown in FIG. 4 with the sealing element therein shown in broken lines.

Referring to FIG. 1, a two piece ostomy pouch includes a mounting portion 10 which is generally rectangular in shape and is made of a semi-rigid hydrocolloid material. Centrally located within the mounting portion 10 is an aperture 12 sized to fit around a stoma of a wearer, not shown. The inner surface 14 of the hydrocolloid mounting portion 10 has adhesive properties which will retain the mounting portion 10 against the skin of the wearer, and the outer surface thereof has an annular ridge 16 extending around the aperture 12 to which an ostomy pouch 18 may be attached.

Figure 2:
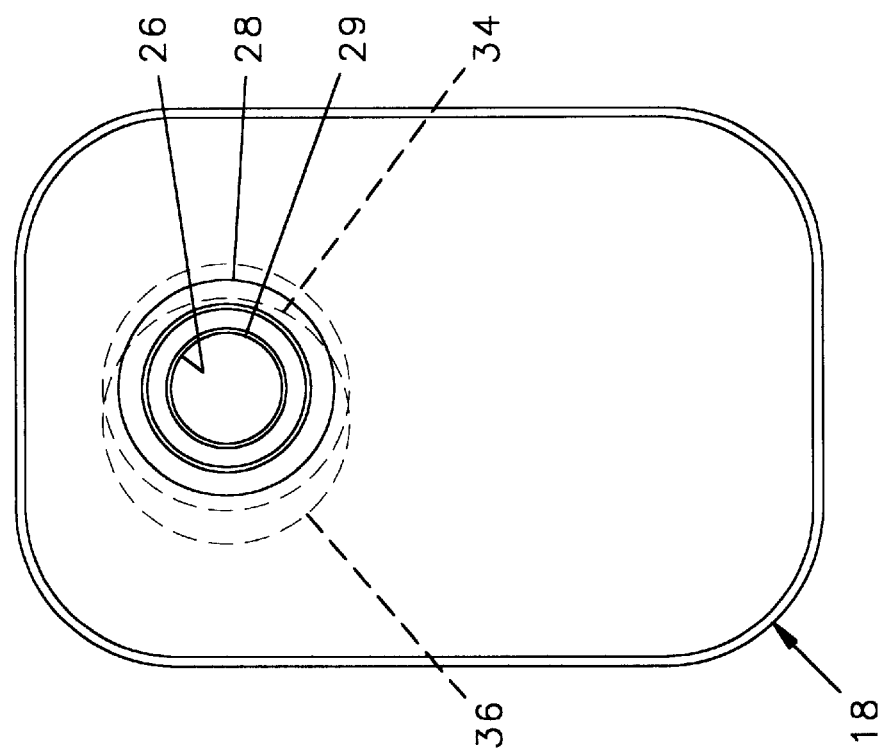
FIG. 2 is a front elevational view of the pouch shown in FIG. 1 with portions of the seal within the pouch shown in broken lines.

Referring to FIGS. 1 and 2, the ostomy pouch 18 is made from a first panel 20 and a second panel 22 of flexible material which is impervious to water, such as a suitable plastic. The outer edges 23 of the panels 20, 22 are heat sealed to each other to form the pouch 18. Near the upper end of the first panel 20 is an aperture 26 for receiving the discharge of a stoma and extending around the aperture 26 on the outer surface of the panel 20 is an attaching member 28 having an annular groove 29 therein. The groove 29 on the pouch 18 is complementary to the annular ridge 16 on the mounting portion 10 and is sized to sealably and releaseably attach the ostomy pouch 18 to the mounting portion 10 by snapping the annular ridge 16 of the mounting portion 10 into the groove 29 of the attachment member 28.

On the inner surface of the first panel 20 and extending around the annular attachment member 28 is an annular flange 30 having a concave inwardly facing wall 32. Around the outer circumference of the annular flange 30 is an annular groove 34. On the inner surface of the second panel 22 is an annular sealing ring 36, the diameter and dimensions of which are sized to sealingly fit within the groove 34 on the inner surface of the first panel 20.

To dispose of the ostomy pouch 18, a user can seal the annular sealing ring 36 into the groove 34 while the pouch 18 is retained to the mounting portion 10. Once the annular ring 36 is sealed into the groove 34, the contents of the pouch cannot escape through the aperture 26 and the pouch can be removed from the mounting portion 10 without causing the release of odors or the contents thereof. Any feces attached to the sealing ring 36 or in the groove 34 during the sealing process will be caught within the concave wall 32 of the annular flange 30 and not be discharged through the aperture 26. The removal and disposal of the pouch 18 can, therefore, be undertaken with a minimum of inconvenience to the wearer. In the preferred embodiment the annular ring 36 is positioned on the inner surface of the second panel 22 such that it is not immediately adjacent to the annular groove 34, but instead is somewhat offset from the position of the annular groove 34 as shown in broken lines in FIG. 2. The offset of the groove 34 with respect to the ring 36 prevents the sealing parts from becoming unintentionally engaged while the pouch is being worn.

Referring to FIG. 3, the present invention may also be embodied in a single piece ostomy pouch 40. In this embodiment, the pouch 40 includes a generally rectangularly shaped mounting member 42 made a hydrocolloid material having adhesive properties as described above. Extending through the center of the mounting portion 42 is an aperture 46 for fitting around a stoma of a wearer.

The ostomy pouch includes a first flexible panel 48 and a second flexible panel 50 heat sealed at the outer edges to the first panel 48 to form the retention portion of the pouch 40. The first panel 48 has an aperture therein which is aligned with the aperture 46 of the mounting portion 42 such that waste products passing from the stoma will enter the interior of the pouch 40. Surrounding the aperture on the inner surface of the first panel 48 is an annular flange 54 made of a suitable material such as plastic or the like, and the inner surface of the flange 54 forms an annular concave surface 56 as shown. Extending around the outer circumference of the flange 54 is an annular sealing groove 58. The inner surface of the second panel 50 has an annular sealing ridge 60 thereon and the ridge 60 has a diameter and other dimensions sized to sealingly fit within the groove 58 to thereby seal the contents of the pouch 40 from escaping through the aperture 46. The annular ride 60 is offset with respect to the groove 58 to prevent the seal from becoming unintentionally engaged, as described above.

Figure 4:
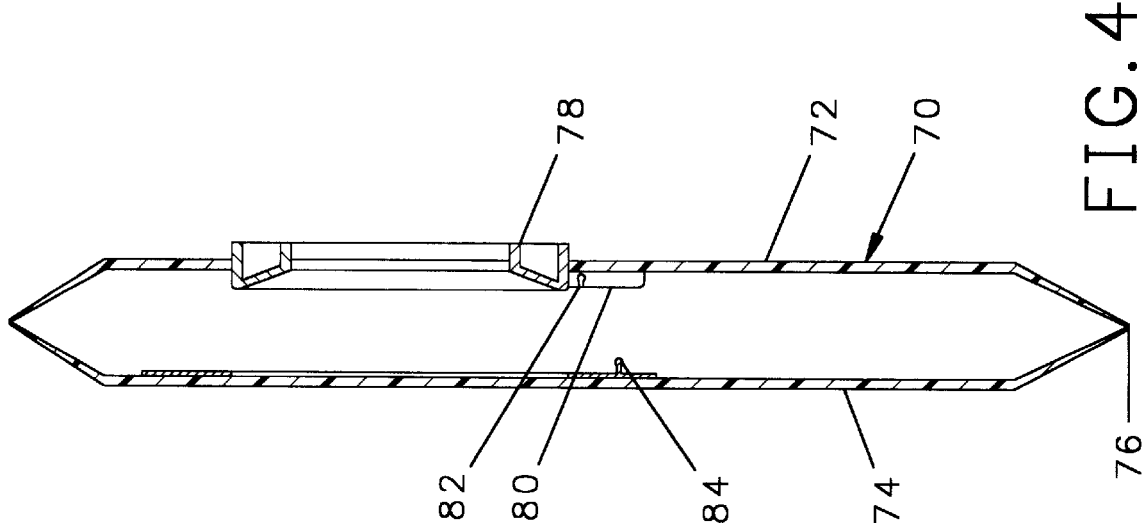
FIG. 4 is a cross sectional view of a two piece ostomy pouch incorporating a second embodiment of the present invention.

Referring to FIGS. 4 and 5, in which a second embodiment of a two piece ostomy pouch 70 is depicted, the pouch 70 is suitable for attachment to the mounting portion 10 depicted and described above with respect to the first embodiment of the ostomy pouch 18. The ostomy pouch 70 has a first panel 72 of flexible material and a second panel 74 of a flexible material, the edges 76 of which are sealed to each other to form the pouch 70. The pouch 70 also has an annular attachment member 78 which is complimentary in shape to the annular ridge 16 for retaining the pouch 70 to the mounting portion 10.

In accordance with the invention, within the inner surface of the first panel 72 is a plastic sealing member 80 having a groove 82 therein. Along the inner surface of the second panel 74 is a ridge 84 having dimensions which are complimentary to the inner dimension of the groove 82 such that the ridge 84 can be snapped into the groove 82 to retain the contents of the pouch in the lower portion thereof.

As best shown in FIG. 5, in the preferred embodiment the ridge 84 is not aligned with the groove 82 such that the ridge 84 on panel 74 cannot be inadvertently sealed into the groove 82 on the panel 72 while the pouch 70 is in use by the wearer, thereby preventing the pouch from becoming inadvertently sealed while being worn.

While the present invention has been described with respect to two embodiments, it will be appreciated by those familiar with the art that many modifications and variations may be made without departing from the true spirit and scope of the present invention. It is therefore the intent of the appended claims to cover all such variations and modifications which fall within the true spirit and scope of the invention.

What is claimed is:

1. An ostomy pouch for receiving human waste products from a stoma comprising a first flexible panel having a first side, a second side, and an outer edge, a second flexible panel having a first side and an outer edge, at least a portion of said outer edge of said first panel joined to said outer edge of said second panel to form a pouch, said first panel having an aperture therein whereby human waste products from said stoma may be received in said pouch, a first annular sealing means on said first side of said first panel and extending around said aperture, a second annular sealing means on said first side of said second panel, said first sealing means and said second sealing means for sealing against each other and for preventing said waste products in said pouch from escaping out said aperture, and a means on said second side of said first panel for attaching said pouch against the body of a wearer with said aperture around a stoma of said wearer.

2. An ostomy pouch in accordance with claim 1 wherein said first sealing means is one of a ridge and groove, and said second sealing means is the other of a ridge and a groove.

3. An ostomy pouch in accordance with claim 1 wherein said means for attaching said pouch against the side of a wearer comprises a mounting portion having a first side and a second side, said first side having an adhesive surface for retaining said mounting portion to the skin of a wearer, said mounting portion having an aperture therein through which the discharge of a stoma may pass, attachment means on said second side of said mounting portion for releasably retaining said ostomy pouch thereto, and means on said pouch for releasable engagement with said attachment means.

4. An ostomy pouch in accordance with claim 1 wherein said first sealing means extends across said first side of said first panel and said second sealing means extends across said first side of said second panel and the engagement of said first sealing means and said second sealing means seals an upper portion of said pouch from a lower portion of said pouch.

5. An ostomy pouch for receiving human waste products from a stoma comprising a first flexible panel having a first side, a second side, and an outer edge, a second flexible panel having a first side and an outer edge, at least a portion of said outer edge of said first panel joined to said outer edge of said second panel to form a pouch, said pouch having an aperture therein whereby human waste products from said stoma may be received in said pouch, a first sealing means extending across said first side of said first panel, a second sealing means extending across said first side of said second panel, said first sealing means and said second sealing means for sealing against each other and for preventing said waste products in said pouch from escaping out said aperture, at least a portion of said first sealing means offset with respect to said second sealing means wherein said first sealing means cannot be inadvertently sealed against said second sealing means, and means for attaching said pouch against the body of a wearer.

6. An ostomy pouch in accordance with claim 5 wherein said means for attaching said pouch against the side of a wearer comprises a mounting portion having a first side and a second side, said first side having an adhesive surface for retaining said mounting portion to the skin of a wearer, said mounting portion having an aperture therein through which the discharge of a stoma may pass, attachment means on said second side of said mounting portion for releasably retaining said ostomy pouch thereto, and means on said pouch for releasable engagement with said attachment means.

* * * * *